United States Patent [19]
Hussein

[11] Patent Number: 6,053,924
[45] Date of Patent: Apr. 25, 2000

[54] DEVICE AND METHOD FOR TRANS MYOCARDIAL REVASCULARIZATION

[76] Inventor: Hany Hussein, 3303 Harbor Blvd., Unit D-13, Costa Mesa, Calif. 92626

[21] Appl. No.: 09/302,046

[22] Filed: Apr. 29, 1999

Related U.S. Application Data

[60] Continuation-in-part of application No. 09/098,013, Jun. 15, 1998, which is a division of application No. 08/739,724, Nov. 7, 1996, Pat. No. 5,810,836
[60] Provisional application No. 60/084,389, May 6, 1998.

[51] Int. Cl.$^7$ ....................................................... A61F 11/00
[52] U.S. Cl. ........................................... 606/108; 606/185
[58] Field of Search .................................. 606/108, 185, 606/167, 170, 180, 198; 623/1, 12; 128/898

[56] References Cited

U.S. PATENT DOCUMENTS

| | | | |
|---|---|---|---|
| 5,287,861 | 2/1994 | Wilk | 128/898 |
| 5,989,278 | 11/1999 | Mueller | 606/167 |

Primary Examiner—Michael Buiz
Assistant Examiner—Kevin Truong
Attorney, Agent, or Firm—James G. O'Neill

[57] ABSTRACT

A medical device and method are described for performing Trans Myocardial Revascularization (TMR) in a human heart. The device consists of a myocardial implant and a directable intracardiac catherter that are suited for delivery into a heart wall of the implant. The catheter utilizes a percutaneous, minimally-invasive access to reach the inner surface of the heart chambers. The catheter provides a conduit for advancing multiple myocardial implants to the heart wall. The implant may include anchoring elements or a retainer for holding the implant body into the heart wall. The implant may include a tapered leading end, and can be advanced into the heart wall using a rotational or a pushing technique until the implant is fully deployed. The implant is then released from the catheter, and another implant inserted into the catheter, or the catheter withdrawn from the human body. The myocardial implant is used to stimulate the formation of new blood vessels (angiogenesis) in the treated heart wall, and to result in Trans Myocardial Revascularization of this heart wall.

16 Claims, 22 Drawing Sheets

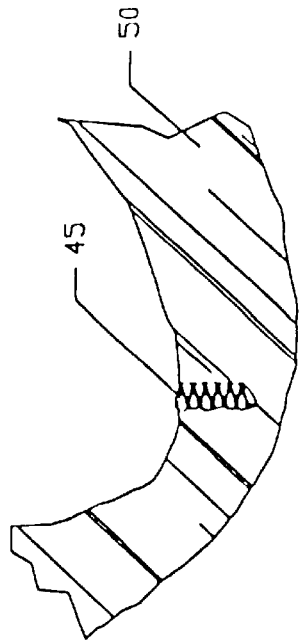
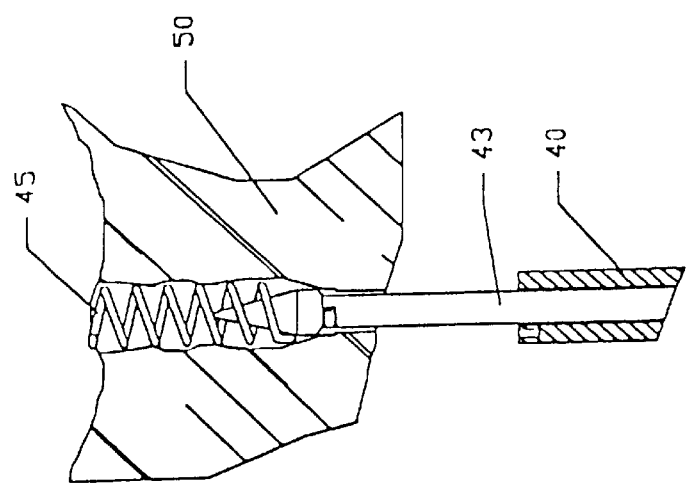
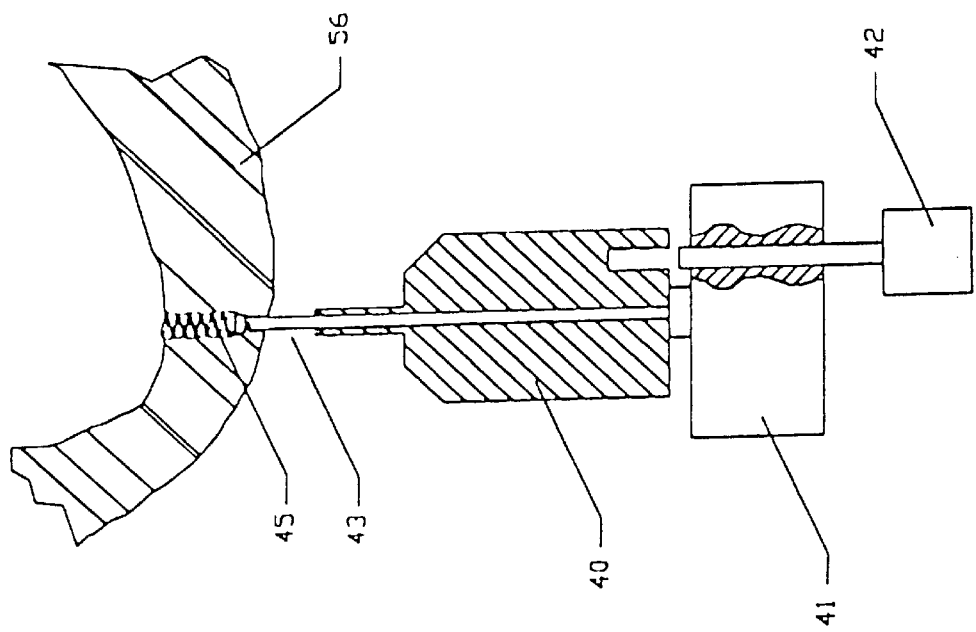
FIGURE 8I
FIGURE 8H
FIGURE 8G

DEVICE AND METHOD FOR TRANS MYOCARDIAL REVASCULARIZATION

CROSS REFERENCE TO RELATED APPLICATIONS

This application claims the benefit of provisional application Ser. No. 60/084,389, filed May 6, 1998, and is a continuation-in-part of pending application Ser. No. 09/098,013, filed Jun. 15, 1998 now pending, which was a divisional application of Ser. No. 08/739,724, filed Nov. 7, 1996, now U.S. Pat. No. 5,810,836.

BACKGROUND OF THE INVENTION

1. Technical Field

This invention is generally directed to the fields of cardiac surgery and interventional cardiology, and particularly, to implants, catheters and methods suited for improving blood flow to a heart muscle and the formation of new blood vessels by Trans Myocardial Revascularization (TMR).

2. Description of Related Art

Symptomatic occlusive coronary artery disease that does not respond to medical or interventional treatment is a major challenge for cardiac surgeons and cardiologists. The discovery of sinusoidal communications within the myocardium (Wearns, 1993) has motivated researchers to attempt various methods for myocardial revascularization based on the existence of this vascular mesh network. These methods aimed at the delivery of oxygenated blood to the vicinity of the sponge-like sinusoidal plexus in order to restore blood flow to the ischemic myocardium. Several investigators have attempted to deliver oxygenated blood directly from the left ventricle into the myocardial sinusoids by employing needle acupuncture to create transmural channels. Trans Myocardial Revascularization (TMR) has been employed clinically (Mirhoseini, 1991) by utilizing a CO2 laser for creating transmural channels in the left ventricular myocardium. These channels are typically 1 mm in diameter and extend throughout the wall thickness (15 to 20 mm) of the ventricle. It has been hypothesized that TMR works by providing a fluid conduit for oxygenated blood to flow from the endocardiac surface (heart chamber) to the mycardium inner layers thus providing oxygenated blood to myocardial cells without requiring coronary circulation; as in reptiles. Animal studies in the canine model have demonstrated the feasibility of this approach. In these studies, an increase in survival rate was demonstrated in dogs that had transmural channels and ligated coronary arteries.

While clinical studies have demonstrated improvements in patient status following TMR, histological studies indicate that the channels created for TMR tend to close shortly after the procedure. Randomized, prospective clinical trials are underway to examine the merit of TMR compared to medical treatment. In the meantime, research studies are being initiated to provide an understanding of the mechanism by which TMR actually works.

It would be desirable to develop means for maintaining the patency of TMR channels or producing new blood vessels within the myocardium. Furthermore, it would be desirable to create channels for TMR without requiring the use of an expensive and bulky laser system, such as currently available CO2 laster systems. This invention provides the desired means for producing trans myocardial channels that are likely to remain patent, and that do not require laser application for generating these channels.

Specifically, the objective of the present invention is to generate needle-made channels or space in the ischemic heart wall, and to deliver or place in these channels (or space) an array of TMR implants in order to provide improved means for supplying blood nutrients to ischemic myocardial tissue. Nutrients flow to the channels having implants therein from the ventricular cavity help to form new blood vessels, and may diffuse from the side ports of the TMR implant to the myocardial tissue through the needle-made channels. The disclosed TMR approach of producing needle-made, implanted channels is supported by the recent scientific evidence (Whittaker et al, 1996) that needle-made transmural channels can protect ischemic tissue. Whittaker et al. assessed myocardial response at two months to laser and needle-made channels in the rat model, which has little native collateral circulation. They found that channels created by a needle can protect the heart against coronary artery occlusion, and that these channels provide greater protection to ischemic tissue than channels created by laser. The limitation of needle-made channels is early closure (Pifarre, 1969). The implanting approach of the present invention offers a possible solution to the early closure problem, while taking advantage of simple and effective means for inserting such TMR implants.

SUMMARY OF THE INVENTION

This invention provides TMR implants and catheter means for creating and maintaining a patent lumen or new blood vessels in the diseased myocardium. The TMR implants of the present invention provide a conduit for the flow of blood nutrients from the ventricular chamber to the intramyocardial vascular network, and a continuous stimulus for the formation of new blood vessels (angiogenesis). These TMR implants can be used as the sole therapy or as an adjunctive therapy to other forms of TMR.

Revascularization of the myocardium can be achieved and maintained by surgical or percutaneous placement in the myocardium of TMR implants.

Various configurations of the TMR implants are disclosed. Manual or powered catheter devices are disclosed for the delivery or placement of stents into a heart wall. The TMR implant can be designed so as to maintain an adequate pressure gradient between the left ventricle and the myocardial tissue in order to maintain the flow from the ventricular cavity to the myocardial tissue of blood nutrients.

Furthermore, the disclosed TMR implants define a cavity which can be pressurized during operation so as to enhance the flow of blood to myocardial tissue.

Several embodiments of the TMR implants and catheter delivery systems therefor are proposed. The implants can be prestressed or made from memory metal in order to minimize the size of the implants during the insertion process. The various catheter delivery systems are described below.

BRIEF DESCRIPTION OF THE DRAWINGS

FIGS. 8A–8I illustrate an alternate TMR stent and a delivery system for insertion of this TMR stent into a heart wall;

DESCRIPTION OF PREFERRED EMBODIMENTS

The following description is provided to enable any person skilled in the art to make and use the invention, and sets forth the best modes contemplated by the inventor of carrying out his invention. Various modifications, however, will remain readily apparent to those skilled in the art, since the generic principles of the present invention have been defined herein specifically to provide for improved myocardial implants and an improved delivery system therefor.

Figure 1:
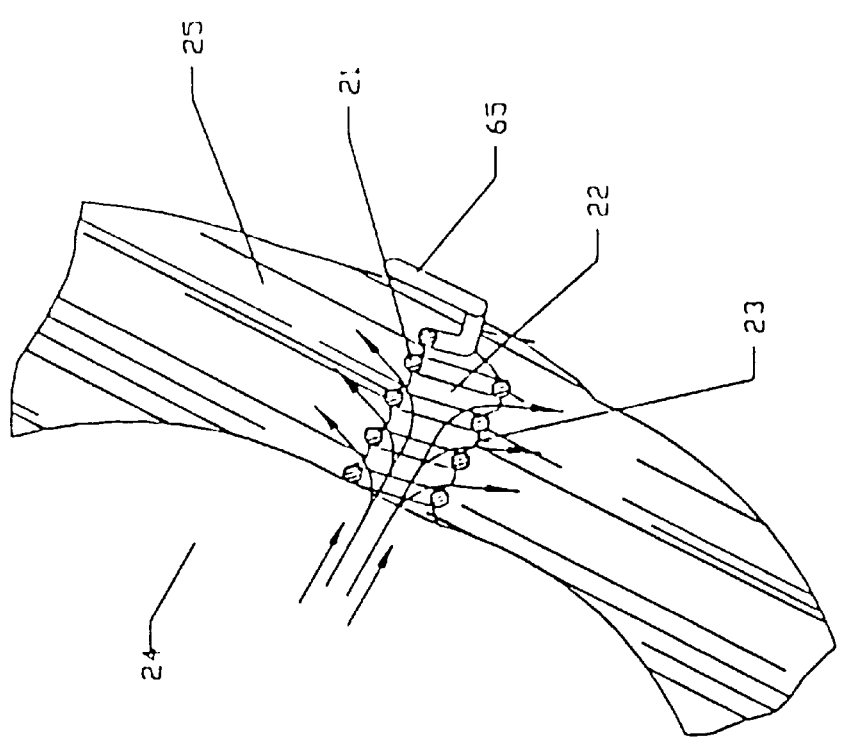
FIG. 1 is a cross-sectional view of a TMR stent inserted in a heart wall. The stent is configured as an expandable coil spring having an integral anchoring wire.

FIG. 1 shows a flexible TMR stent (hereinafter "myocardial implant") having a coil spring body 21 defining a cavity 22 and spacing 23 between the turns of said spring body. In this embodiment, blood nutrients flow from the heart chamber 24 to the heart wall 25 by passage through the coil spring cavity 22 and spacing 23. An anchoring wire 65 secures the stent to the heart wall.

Figure 2:
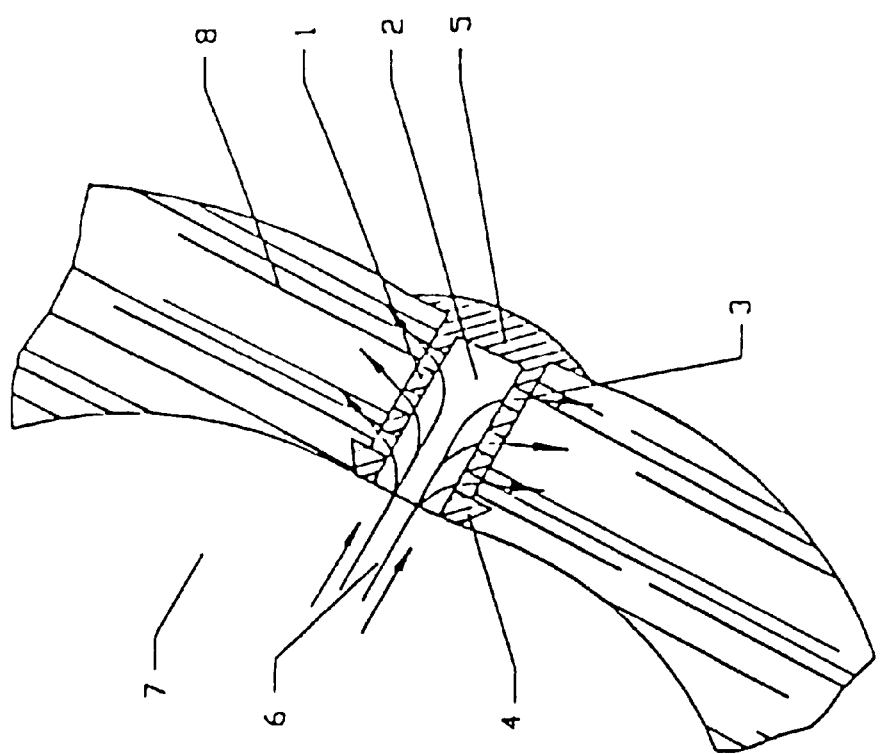
FIG. 2 is a cross-sectional view of a TMR stent having the configuration of a rigid sleeve having side ports.

FIG. 2 shows a myocardial implant that comprises a tubular body 1, cavity 2, side ports 3, retainer 4, and closure 5. In this embodiment, blood nutrients 6 are transported from the heart chamber (ventricle) 7, through the cavity 2 and side ports 3, to the heart wall 8.

Figure 3:
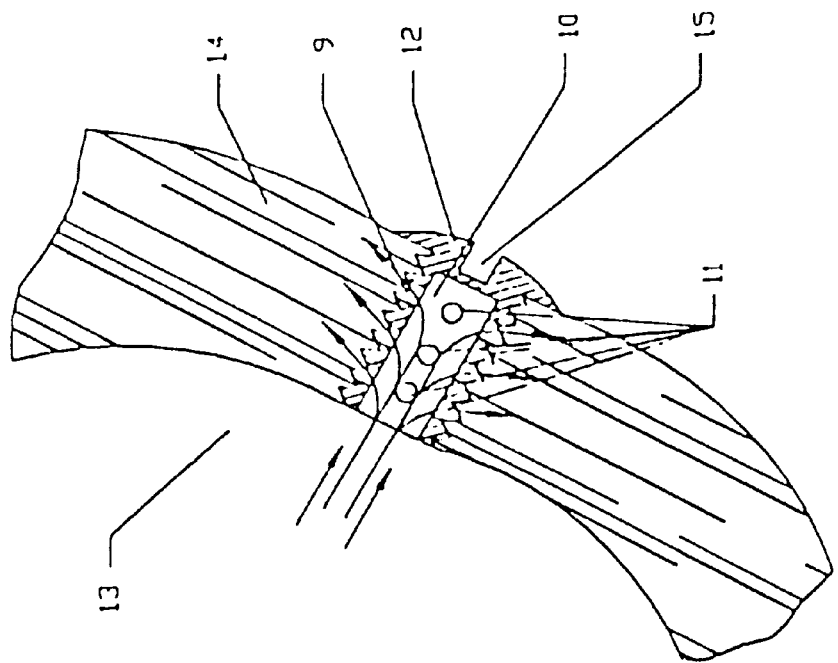
FIG. 3 is a cross-sectional view of a TMR stent having the configuration of a hollow screw with side ports.

FIG. 3 shows a myocardial implant that is configured as a hollow screw having a threaded body 9, cavity 10, side ports 11, closure 12, and slot 15. In this embodiment, blood nutrients flow from the heart chamber 13 to the heart wall 14 by passage through the cavity 10 and side ports 11.

Figure 4:
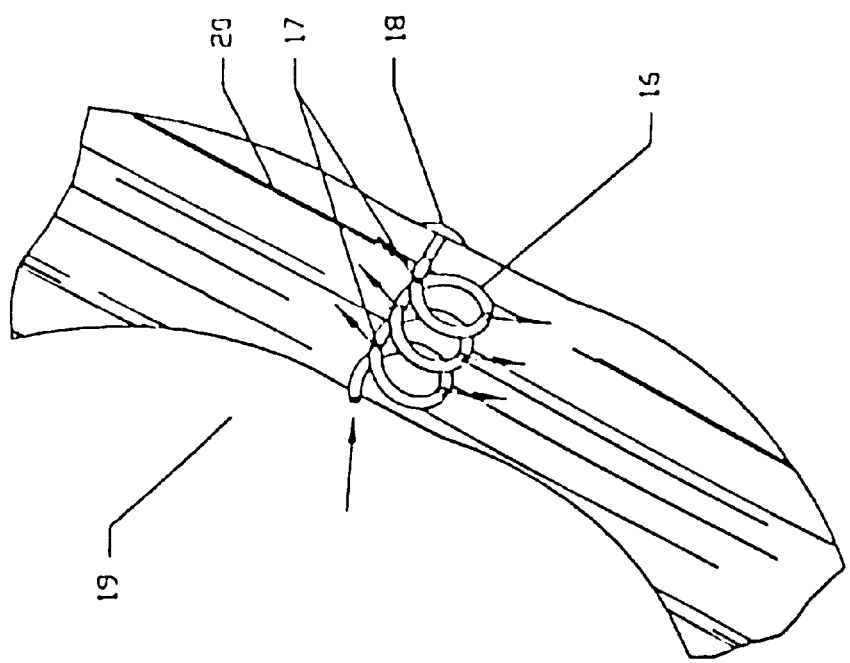
FIG. 4 is a cross-sectional view of a TMR stent having the configuration of a wire screw.

FIG. 4 shows a myocardial implant that is a hollow wire screw having an elongated hollow coil body 16, side ports 17, and anchor 18. In this embodiment, blood nutrients flow from the heart chamber 19 to the heart wall 20 by passage through the hollow core of the wire 16 and side ports 17.

Figure 5:
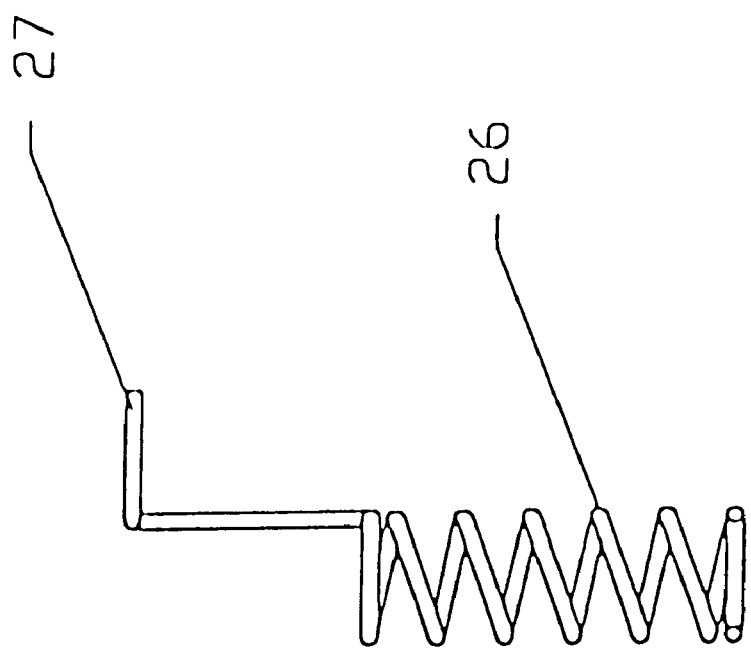
FIG. 5 is a cross sectional view of a flexible stent having an integral anchoring coil.

FIG. 5 shows a flexible myocardial implant having a coil body 26 and an anchoring coil 27 which is an integral part of the myocardial implant. The anchoring coil prevents detachment of the myocardial implant from the heart wall.

Figure 6:
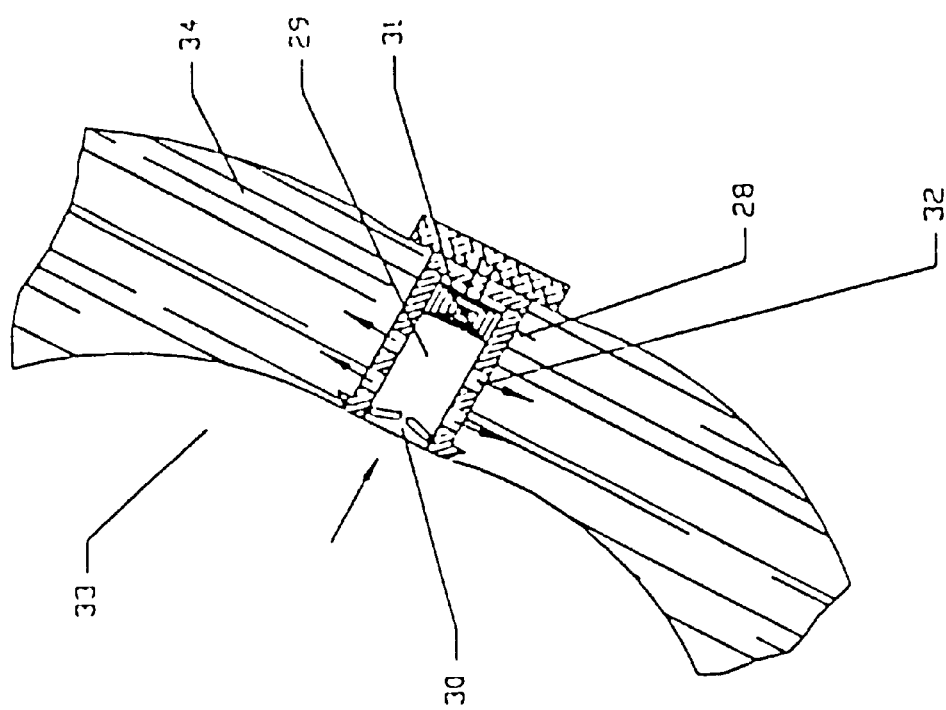
FIG. 6 is a cross-sectional view of a TMR stent having the configuration of a miniature pump.

FIG. 6 shows a myocardial implant having a cylindrical body 28 defining a cavity 29. A valve 30, pumping element 31, and side ports 32 are situated within the cavity 29. In this embodiment, blood nutrients flow from the heart chamber 33 to the pumping cavity 29. The valve 30 is activated and the pumping element 31 operates to displace the blood from the pumping cavity 29 through side ports 32 to the heart wall 34.

Figure 7:
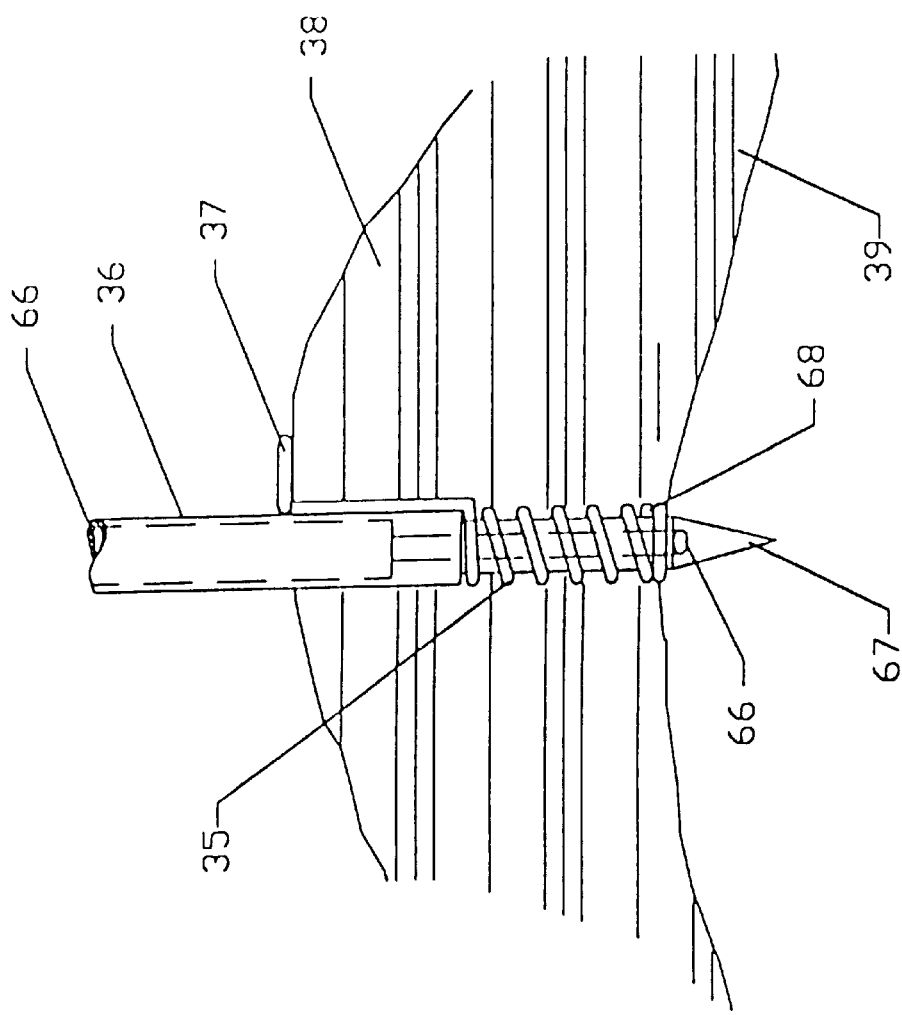
FIG. 7 shows a TMR delivery device and method for insertion of a TMR stent into a heart wall.

FIG. 7 shows the construction and method of use of one embodiment of a delivery device for creating a pathway in the heart wall and for placement of a myocardial implant in this pathway. In this first embodiment, a needle obturator 36 carries a myocardial implant 35 having an anchoring wire 37, which may be offset from the myocardial implant, as shown in FIG. 7, or aligned with the myocardial implant, as shown in FIGS. 18A–22. The obturator and myocardial implant are inserted through the heart wall 38 until the endocardiac surface is reached. After the endocardiac surface 39 of the heart wall is reached, the obturator 36 is removed, as by turning or unscrewing the same, thereby leaving the myocardial implant 35 embedded in the heart wall. Additional improvements include a fluid channel 66 that is formed in the obturator body to provide an indication that the obturator's distal end 67 has crossed the endocardiac surface 39.

Figure 8B:
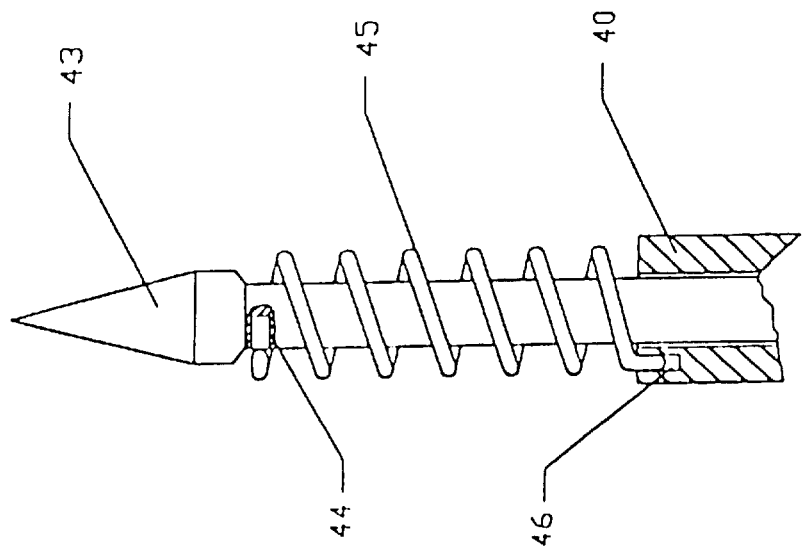
Figure 8A:
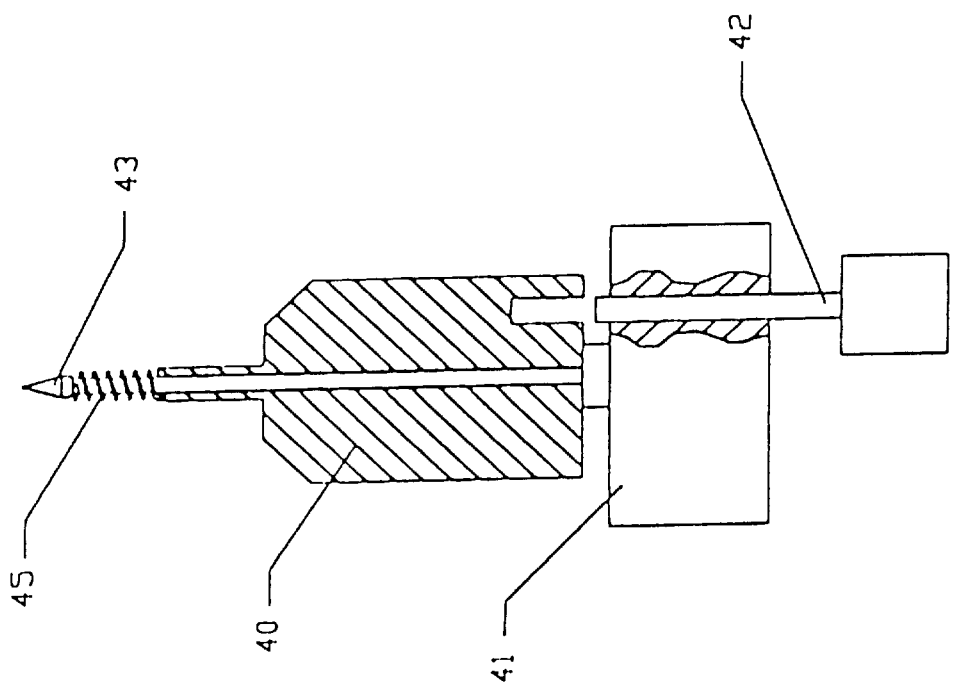

FIGS. 8A through 8I show the construction of an alternate myocardial implant and a second embodiment of a delivery system for placement of the alternate implant in a heart wall. FIG. 8A shows a delivery system having a pin 40 and handle 41 having a locking device 42. An obturator 43 is mounted in the pin 40. The obturator 43 has a recess 44 (FIG. 8B) to engage the distal end of a myocardial implant 45. The pin 40 has a recess 46 (FIG. 8B) to engage the proximal end of the implant 45.

Figure 8D:
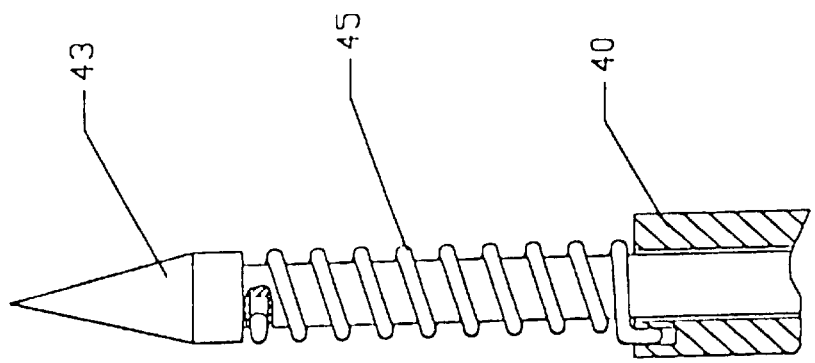
Figure 8C:
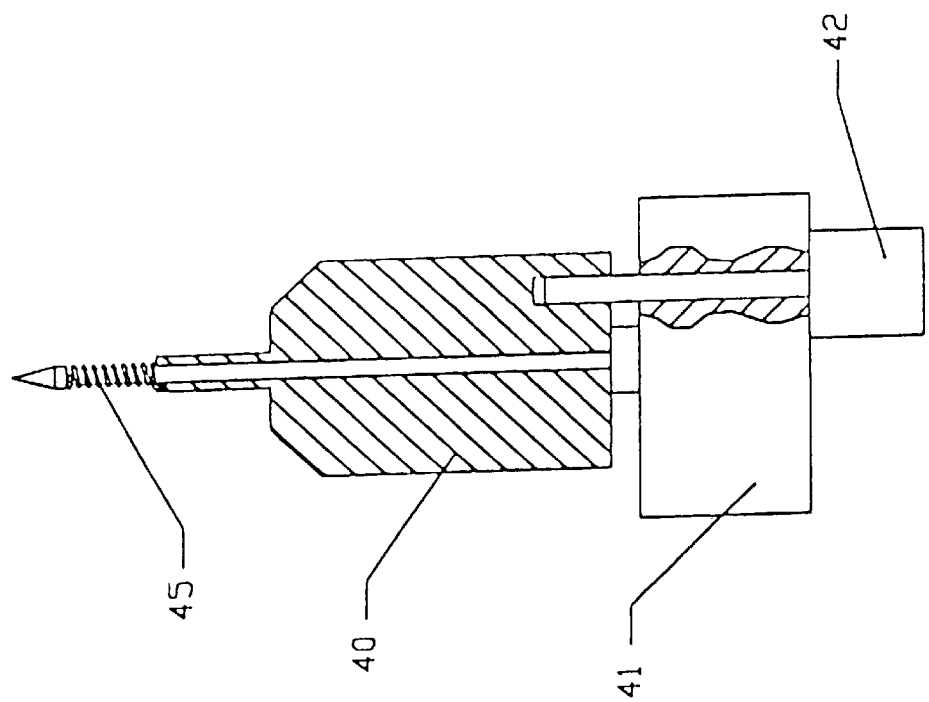
Figure 8F:
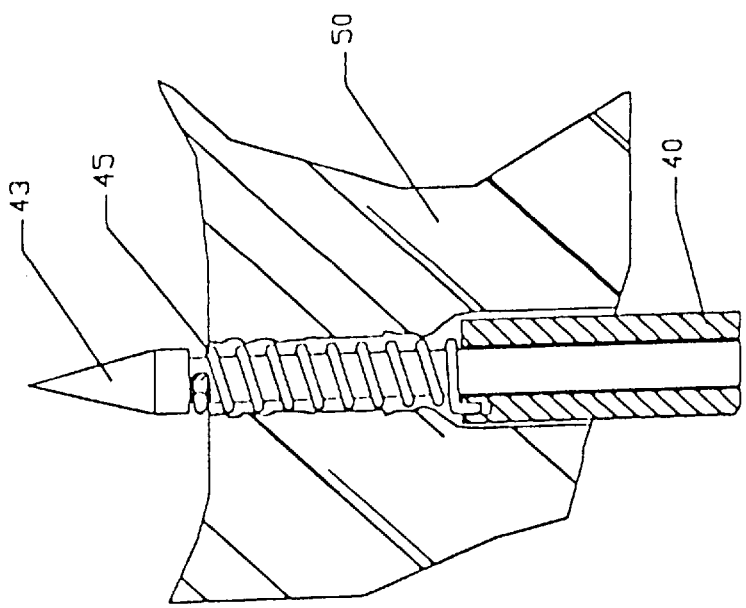
Figure 8E:
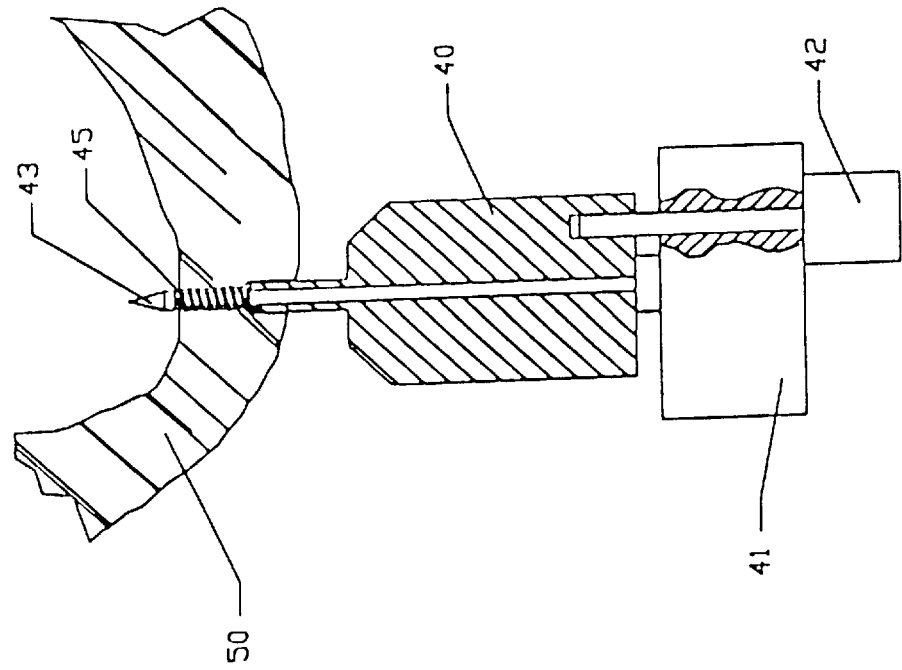

The method of use involves the placement of the implant 45 over an obturator 43. The pin 40 is then rotated to create a radial stress on the TMR device 45 (FIG. 8D). The pin 40 is locked to the handle 41 (FIG. 8C). Advancement through the heart wall 50 of the obturator and TMR device 45 is achieved by pressing the obturator through the heart wall (FIGS. 8E, 8F). The pin 40 is released from handle 41 by withdrawing the locking device 42 (FIGS. 8G, 8H). This causes the implant 45 to be released from the obturator 43. The obturator 43 is then pulled back from the heart wall 50 leaving the implant 45 imbedded in the heart wall (FIG. 8I).

Figure 9:
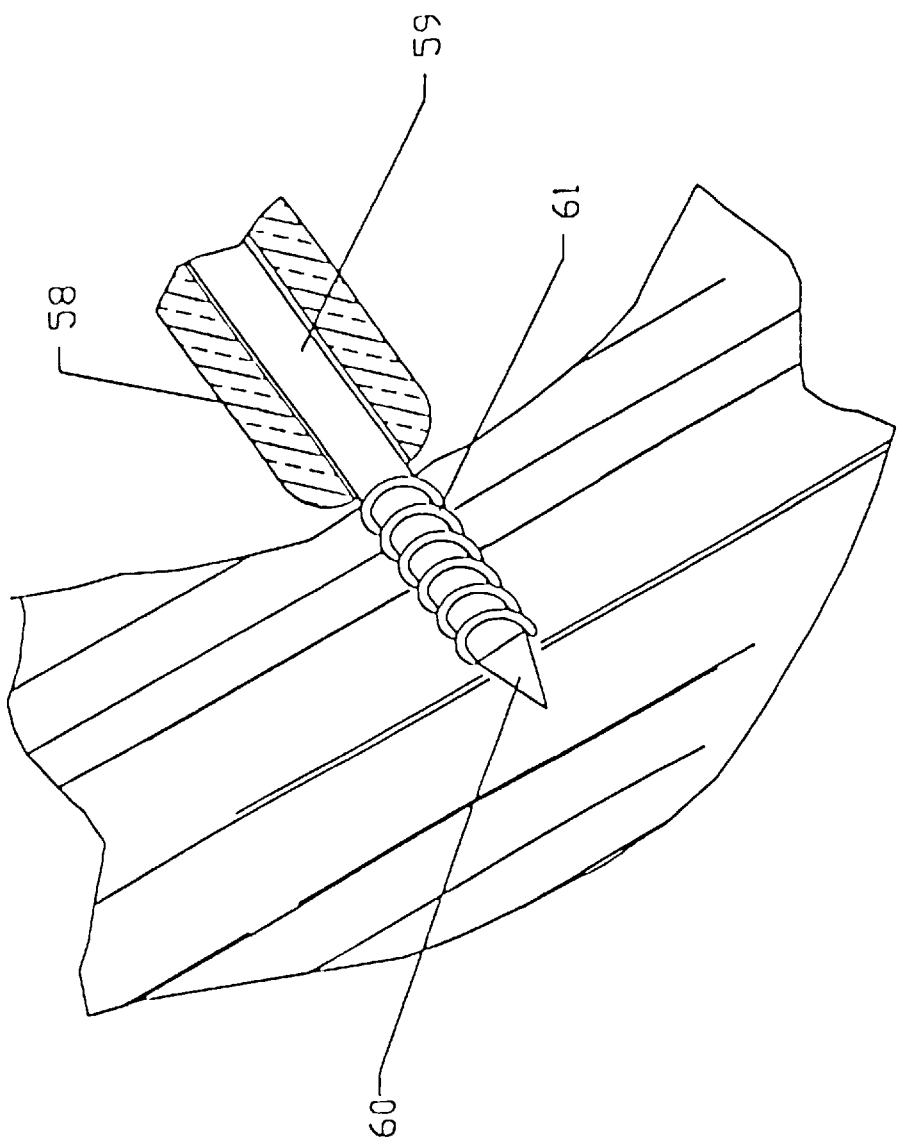
FIG. 9 shows a catheter delivery device and method utilizing a percutaneous access for insertion of a TMR stent into a needle-made space within the heart wall.

FIG. 9 shows a catheter 58 having a slidable wire 59 which terminates at its distal end in a needle point 60. A myocardial implant 61 is mounted proximal to the needle point. Advancing the needle spreads the heart wall tissue and positions the implant 61 into that tissue. Withdrawal of the needle releases the implant 61 in the heart wall.

Figure 10:
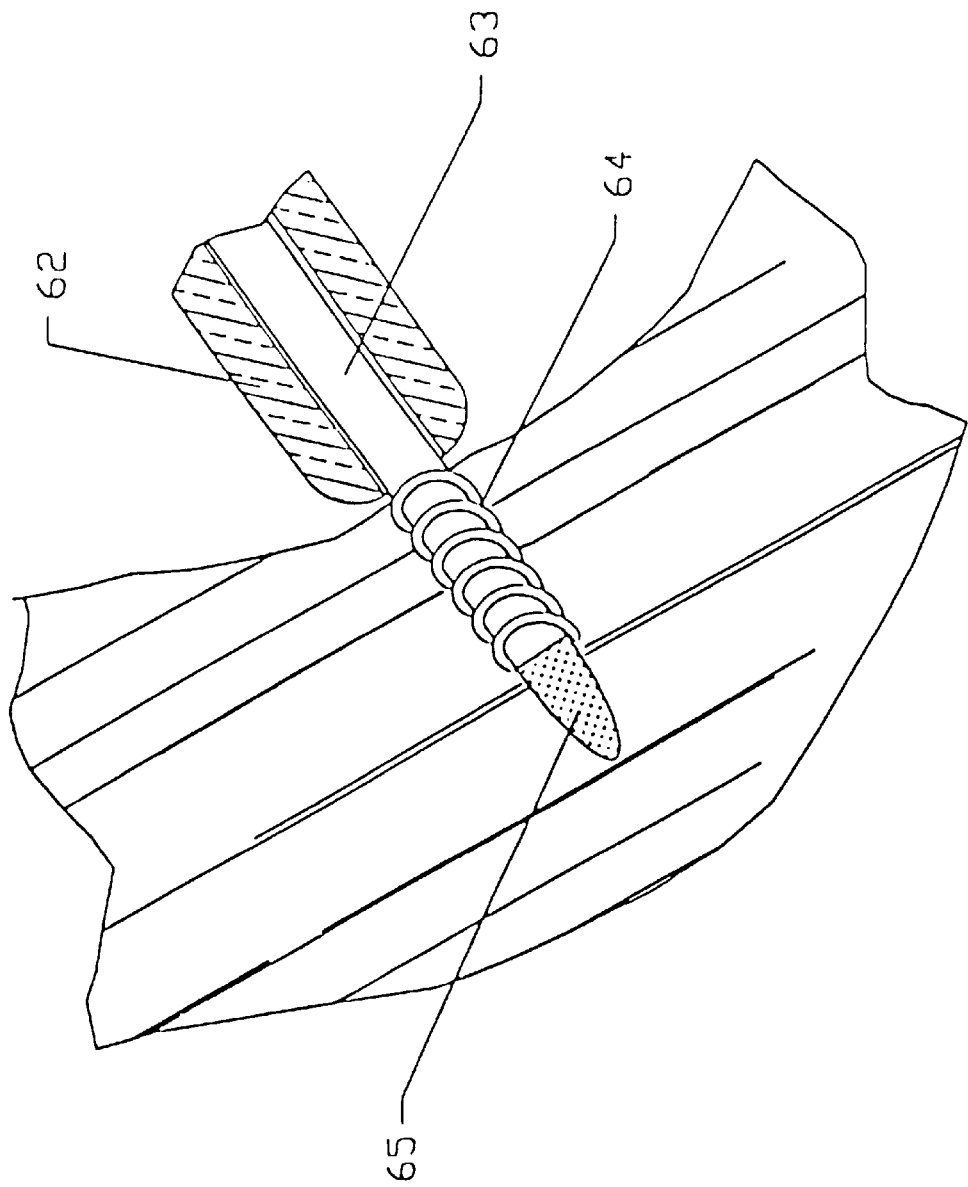
FIG. 10 shows an alternate catheter delivery device and method utilizing a percutaneous access for creating a channel in the heart wall, and for insertion in this channel of a TMR stent.

FIG. 10 shows a catheter 62 which incorporates a slidable wire 63 that terminates at its distal end into a drill or other mechanical attachment 65 for making holes in the heart wall tissue. A myocardial implant 64 is mounted proximal to the drill 65 on the slidable wire 63. Advancing the drilling tool creates a channel in the tissue and positions the implant 64 in this channel. Withdrawal of the drilling tool releases the implant 64 in the heart wall.

The disclosed myocardial implants are expected to incorporate a cavity having a diameter in the range of 1–5 millimeters and a length in the range of 10–30 millimeters. The bodies of the myocardial implants are made of a bio-compatible material; such as stainless steel. The myocardial implants may also be coated with a material that promotes angiogenesis (formation of new blood vessels). The myocardial implants may also be made from carbon, gold, platinum, or other suitable materials.

The number of myocardial implants required of used for each patient depends on the size of the implants and the surface area of the heart segment that is being revascularized. For example, a small segment may require only one myocardial implant, while a large segment may require 10 implants to be implanted in the heart wall.

Turning now to FIGS. 11–20, there shown are alternate embodiments of myocardial implants and a catheter delivery system for implanting such myocardial implants in a heart wall.

Figure 11:
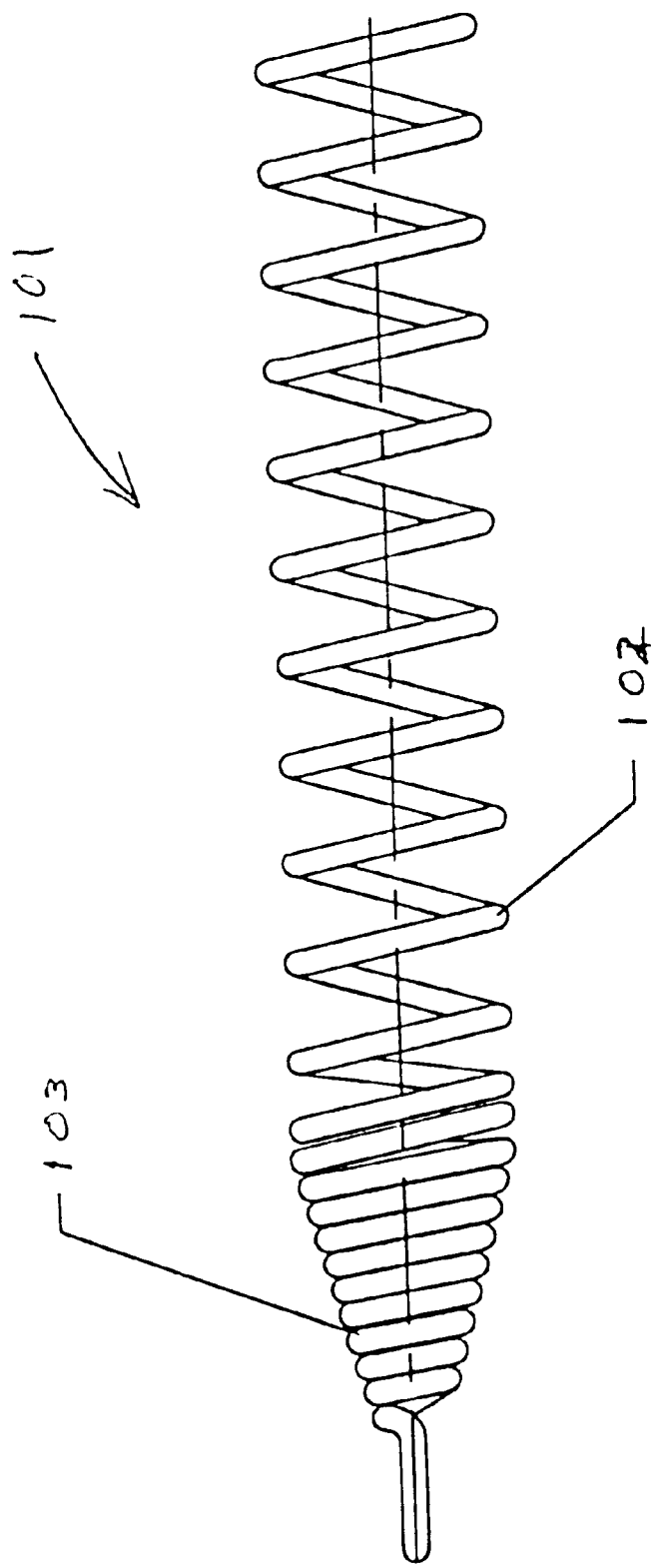
FIG. 11 is a front elevational view of a further embodiment of an implant (myocardial stent)

FIG. 11 shows a preferred embodiment of a myocardial implant 101 having a coil spring body 102 and a tapered leading end 103, which facilitates the placement into a heart wall of the implant 101 without requiring the creation in myocardium of a channel.

Figure 12:
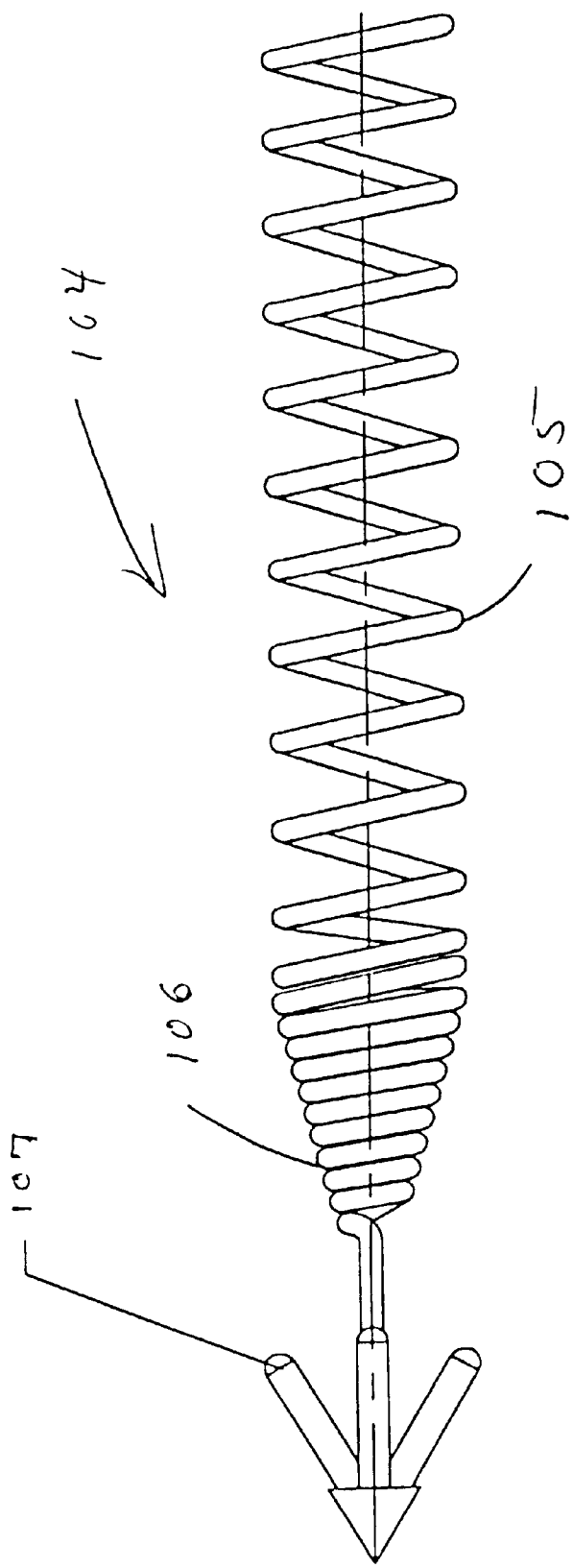
FIG. 12 is a front elevational view of a still further embodiment of a TMR implant.

FIG. 12 shows another preferred embodiment of a myocardial implant 104 having a coil spring body 105 and a tapered leading end 106, which incorporates distal anchor means 107 with a plurality of arms for holding the implant 104 into a heart wall.

Figure 13:
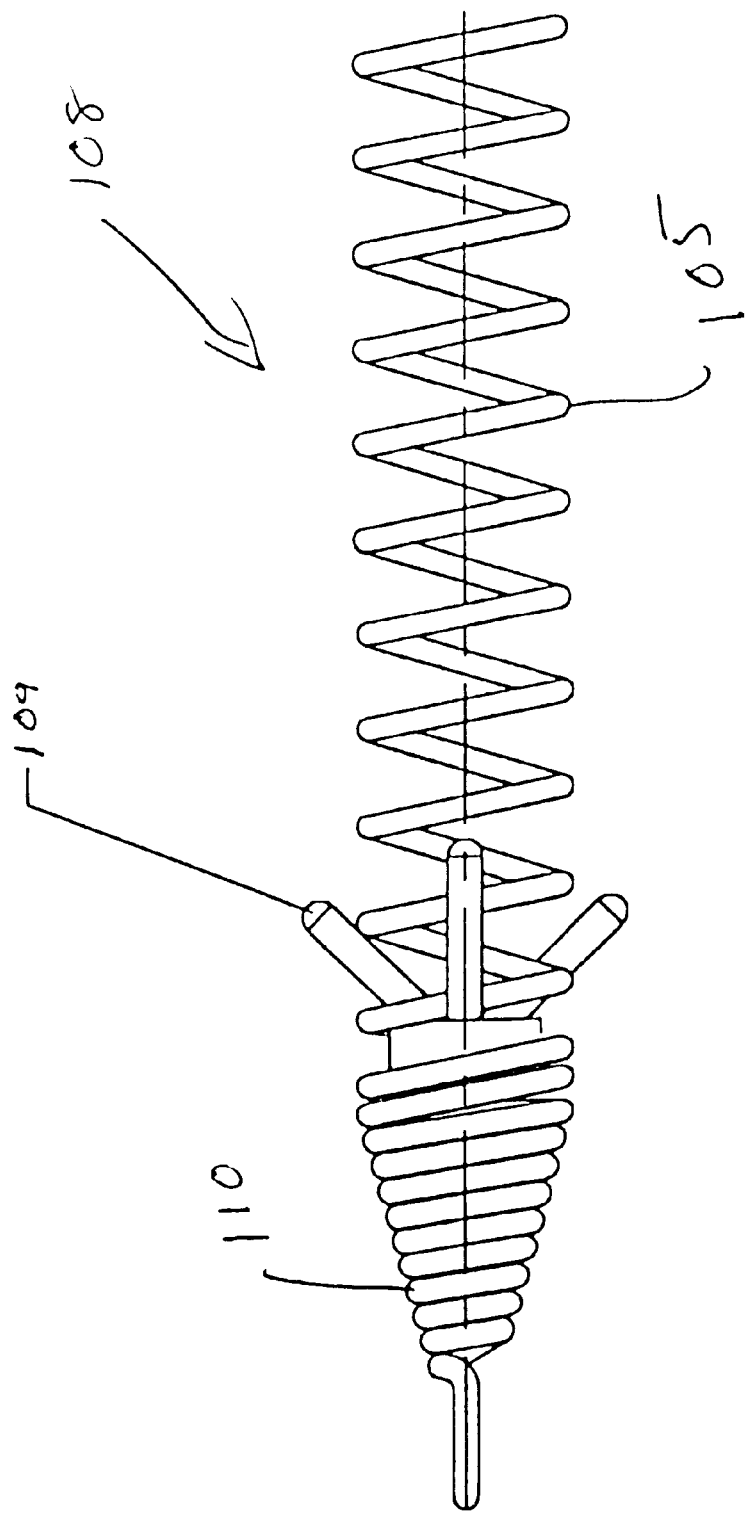
FIG. 13 is a front elevational view of a further embodiment of a TMR implant.

FIG. 13 shows a still further embodiment of a myocardial stent 108 having a coil spring body 105, which incorporates an anchor means 109 having a further plurality of arms located proximal to and before a tapered leading end 110.

Figure 14:
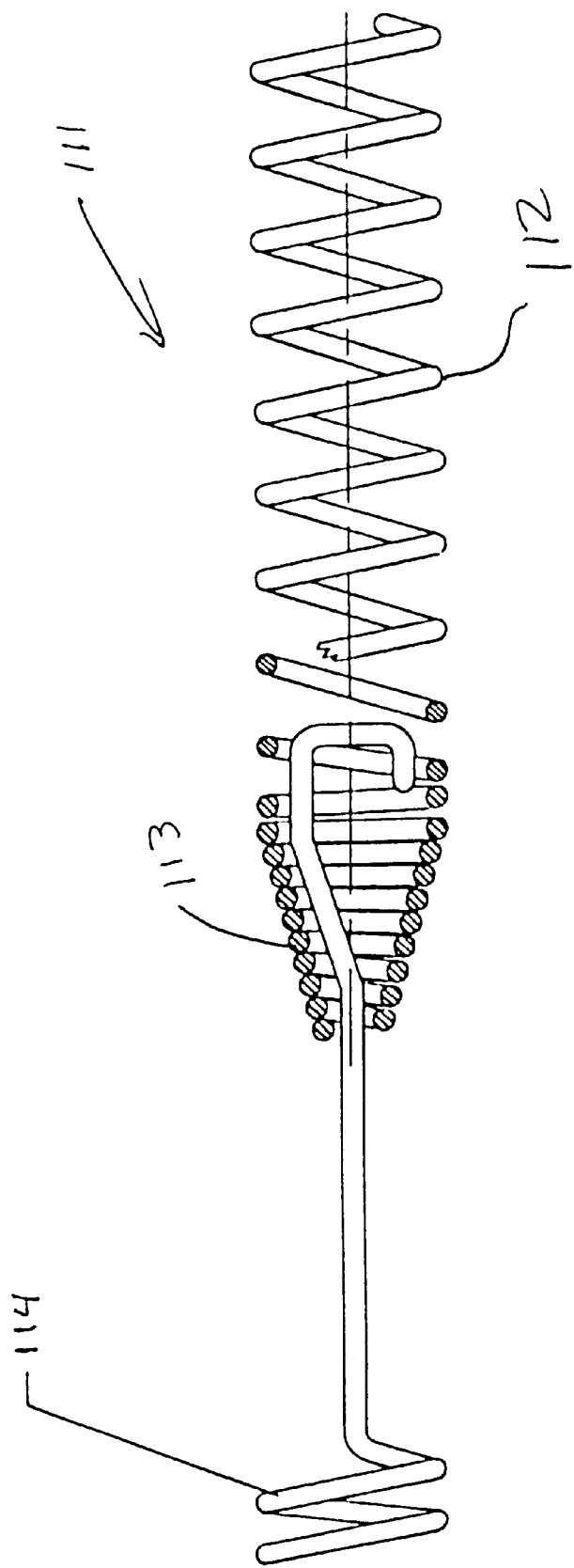
FIG. 14 is a front elevational view, partly in cross section, of an alternate embodiment of a TMR implant.

FIG. 14 shows a further embodiment of a myocardial implant 111, having a coil spring body 112 with a tapered distal end 113, which incorporates a flexible retainer means 114 having a plurality of coaxial rings therein for holding this implant into a heart wall.

Figure 15:
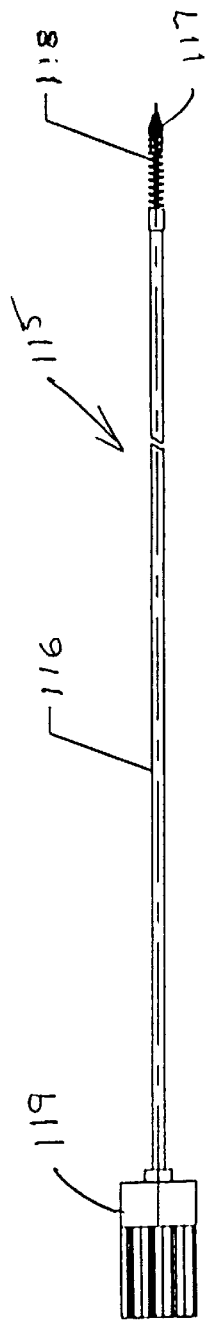
FIG. 15 is a front elevational view of a flexible wire and handle assembly for delivery of an implant.

FIG. 15 shows a preferred embodiment of an inner portion 115 of a myocardial implant delivery system consisting of a flexible shaft body 116, which terminates at its distal end into means for holding 117 a single or multiple implants 118, and at its proximal end into handle means 119.

Figure 16:
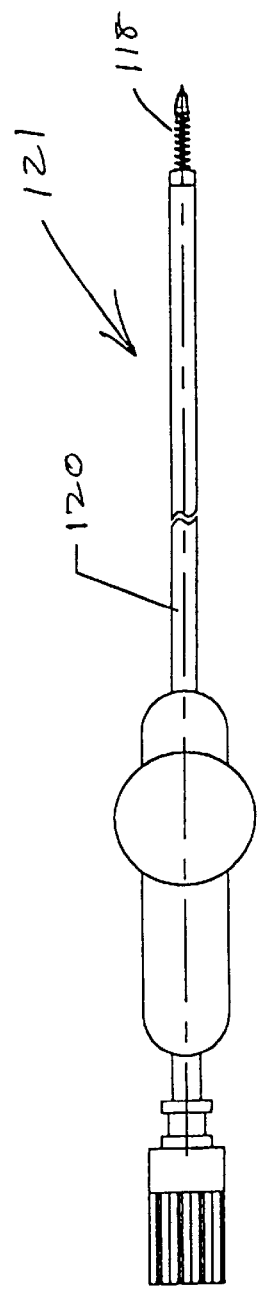
FIG. 16 is a front elevational view of a catheter for holding the wire and handle of FIG. 15, for delivery of an implant to a heart wall.

FIG. 16 shows a preferred embodiment of an outer casing or portion 120 of a myocardial stent delivery system consisting of a flexible guiding catheter 121, which provides means for access and delivery to an inner surface of a heart wall of at least one myocardial implant held on the end 117 of the flexible shaft 116 of FIG. 15.

Figure 17:
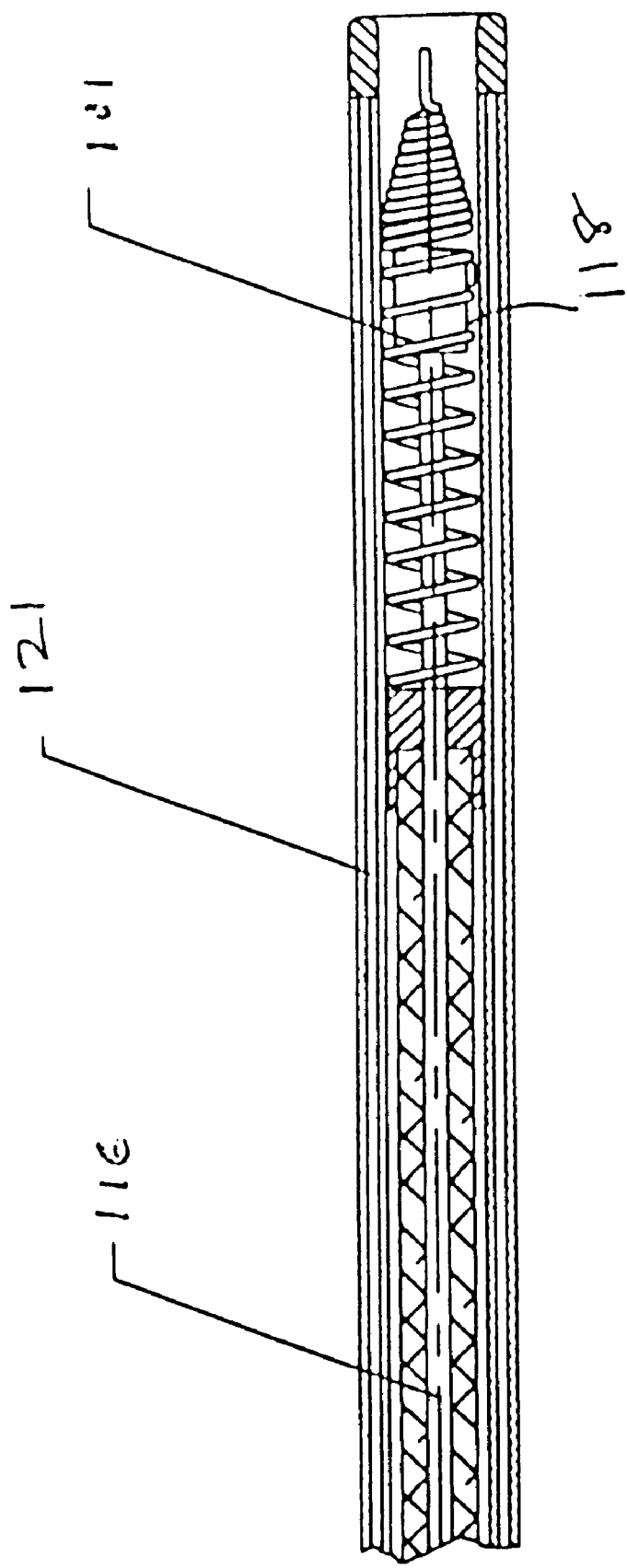
FIG. 17 is an enlarged, partial cross sectional view of the flexible wire end of the device shown in FIG. 15, with a myocardial implant thereon.

FIG. 17 is a partial cross sectional view, showing a myocardial implant 101, mounted on the end 118 of the flexible shaft 116, inserted through flexible guiding catheter 121 in preparation for delivery to heart wall of the implant 101.

Figure 18:
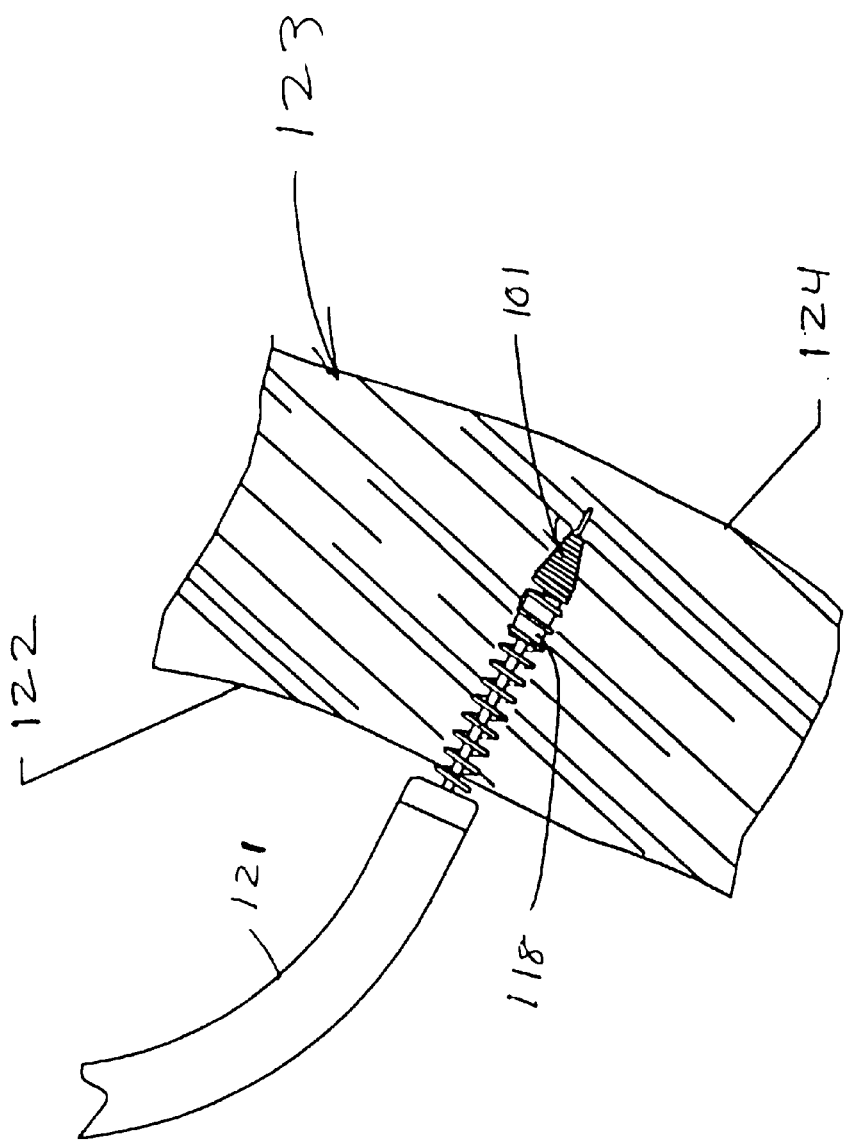
FIG. 18 is a schematic view of the flexible wire shown in FIG. 17, with a myocardial implant mounted on the end, and inserted in a heart wall.

FIG. 18 shows a schematic representation of one method for deployment of a myocardial implant 101 by advancement of such implant from an inner surface 122 of a heart wall 123 towards an outer surface 124 of the heart wall.

Figure 19:
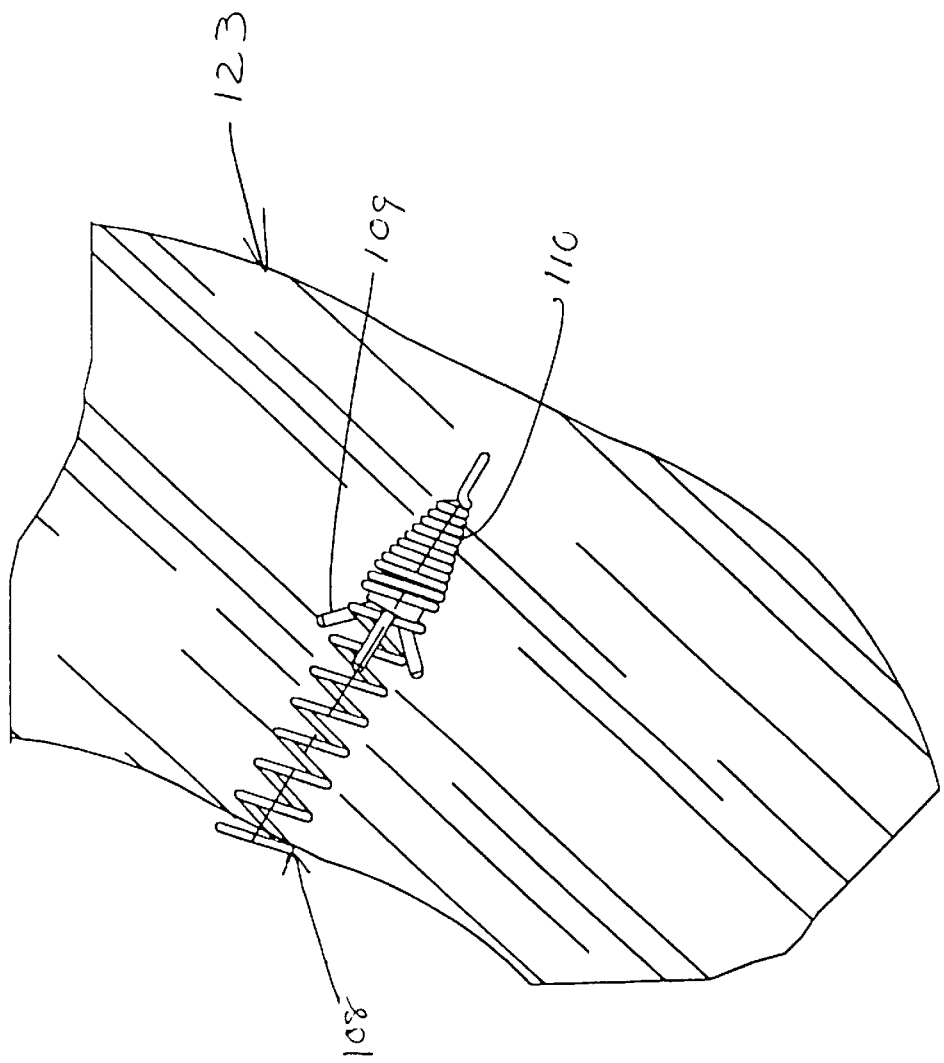
FIG. 19 is a schematic view showing a myocardial implant deployed and anchored in a heart wall.

FIG. 19 shows a myocardial implant 108 deployed and anchored into a heart wall 123, and having the tapered end 110 and the plurality of arms of the anchor means 109 secured in the heart wall.

Figure 20:
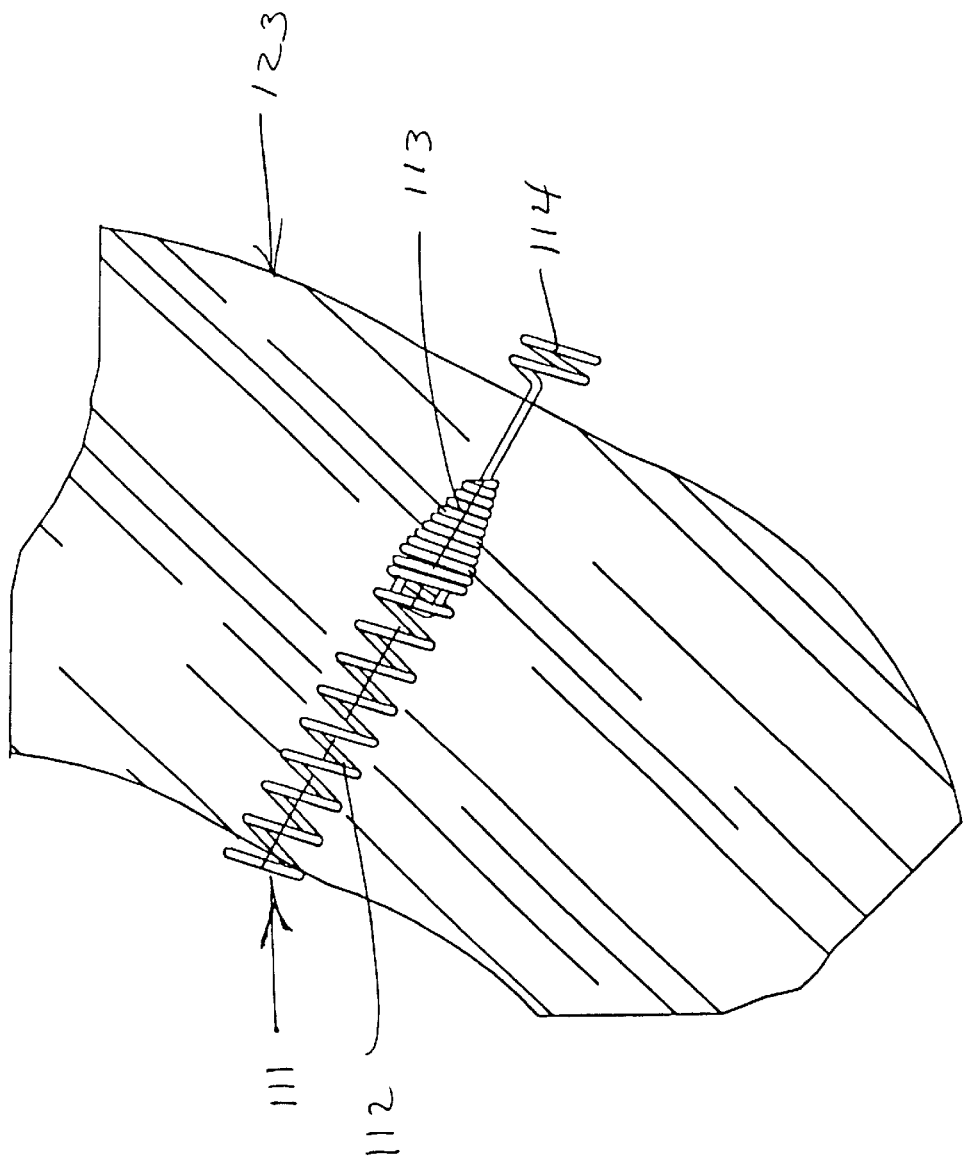
FIG. 20 is a further schematic view showing a further myocardial implant completely inserted through a heart wall.

FIG. 20 shows a myocardial implant 111 implanted into the heart wall 123, and having a tapered end 113 and a flexible retainer means 114.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A myocardial implant for Trans Myocardial Revascularization in a portion of a heart wall, comprising, in combination:

an elongated, flexible, coiled body, having an outside surface, an inside surface, an internal cavity and two ends;

a plurality of openings through the coiled body for connecting the internal cavity to the outside surface; and a tapered leading end formed at one of the two ends, coaxial with the elongated, flexible coiled body, for penetration into a heart wall.

2. The myocardial implant of claim 1, further including an anchoring element at the tapered leading end.

3. The myocardial implant of claim 2 wherein the anchoring element is an outer tip of the tapered leading end.

4. The myocardial implant of claim 3 wherein the anchoring element has a plurality of arms, formed at an angle to the leading end.

5. The myocardial implant of claim 3 wherein the anchoring element has a plurality of rings, and the plurality of rings are spaced from the outer tip of the tapered leading end.

6. The myocardial implant of claim 2 wherein the anchoring element is held between the tapered leading end and the elongated, flexible coiled body.

7. The myocardial implant of claim 6 wherein the anchoring element has a plurality of arms.

8. The myocardial implant of claim 7 wherein the arms are formed at an angle to the leading end.

9. A myocardial implant for trans myocardial revascularization, comprising, in combination:

an elongated, flexible coil spring body, having an outside surface, an inside surface, an internal cavity and two ends;

a plurality of openings connecting the inside surface to the outside surface;

a tapered means formed at a first of the ends for inserting and securing the myocardial implant in a myocardium wall.

10. The myocardial implant of claim 9 wherein the tapered means is a tapered end having an anchoring means associated therewith.

11. The myocardial implant of claim 10 wherein the anchoring means is held in a narrow tip of the tapered end.

12. The myocardial implant of claim 11 wherein the anchoring means extends from the tapered end, away from the flexible, elongated coil spring body.

13. The myocardial implant of claim 12 wherein the anchoring means has a plurality of arms.

14. The myocardial implant of claim 13 wherein the plurality of arms are angled with respect to the tapered end.

15. The myocardial implant of claim 12 wherein the anchoring means is composed of a plurality of coaxial rings.

16. The myocardial implant of claim 11 wherein the anchoring means is a plurality of angled arms held in the tapered end, adjacent the flexible, elongated coil spring body.

* * * * *